United States Patent [19]

Richarz et al.

[11] Patent Number: 4,491,672

[45] Date of Patent: Jan. 1, 1985

[54] PREPARATION OF AROMATIC AZOMETHINES

[75] Inventors: Winfried Richarz, Ludwigshafen; Dietrich Mangold, Neckargemuend; Bjoern Girgensohn, Mannheim, all of Fed. Rep. of Germany

[73] Assignee: BASF Aktiengesellschaft, Fed. Rep. of Germany

[21] Appl. No.: 155,760

[22] Filed: Jun. 2, 1980

[30] Foreign Application Priority Data

Jun. 22, 1979 [DE] Fed. Rep. of Germany ....... 2925263

[51] Int. Cl.$^3$ ............................................. C07C 119/08
[52] U.S. Cl. .................................................. 564/271
[58] Field of Search ...................... 260/566 R; 564/271

[56] References Cited

U.S. PATENT DOCUMENTS 3,835,191  9/1974  Wagner et al. ................. 260/566 R

FOREIGN PATENT DOCUMENTS 1793811  7/1977  Fed. Rep. of Germany .

OTHER PUBLICATIONS

Wagner & Zook, "Synthetic Organic Chemistry", pp. 728–729, (1968), Publ. John Wiley and Sons.
Walker, J. Frederic, "Formaldehyde", 3rd Ed., (1964), pp. 369–371, (Reinhold Publishers. (ACS Monograph Series).
Sprung, Murray M., *Chemical Reviews, vol. 26, (1940), pp. 297–298, 303–304, and 311–315.*
Tollens, *Berichte der deut. chem. Gesellschaft, vol. 17, (1884), pp. 657–659.*

Primary Examiner—Natalie Trousof
Assistant Examiner—L. Hendriksen
Attorney, Agent, or Firm—Keil & Weinkauf

[57] ABSTRACT

Aromatic azomethines are prepared by reacting anilines with formaldehyde and then removing the greater part of the water by distillation, low-boiling alcohols, in certain amounts, being present during the distillation and, if desired, during the reaction or during a part thereof.

The aromatic azomethines obtainable by the novel process are valuable starting materials for the preparation of herbicides, especially pre-emergence herbicides and post-emergence herbicides, fungicides, insecticides, bacteriostatic agents, fungistatic agents and vulcanization accelerators.

7 Claims, No Drawings

PREPARATION OF AROMATIC AZOMETHINES

The present invention relates to a process for the preparation of aromatic azomethines by reacting anilines with formaldehyde and then removing the greater part of the water by distillation, low-boiling alcohols, in certain amounts, being present during the distillation and, if desired, during the reaction or during a part thereof.

German Published Application DAS No. 1,793,811 discloses that aromatic azomethines may be prepared by reacting anilines with formaldehyde. To achieve a high yield of end product, the water liberated is removed continuously from the reaction mixture, during the reaction, by means of an azeotropic entraining agent. The latter is preferably an aromatic hydrocarbon, eg. benzene, toluene or a xylene, but may also be an aliphatic solvent, eg. heptane or cyclohexane. Preferably, the reaction is carried out with an excess of formaldehyde, in order to compensate for losses of formaldehyde which occur on azeotropic removal of the water of reaction from the mixture. After completion of the reaction, ie. as soon as no further formation of water is observed, the product is purified, preferably by distillation under reduced pressure. As is shown by all the Examples and by the description, the reaction is carried out in the presence of a base, and using a large excess of formaldehyde. It is pointed out that the continuous removal of water must specifically be carried out during the reaction; the publication describes the reaction with simultaneous azeotropic distillation or with simultaneous removal of the water by means of a water absorbent. In all the Examples, large amounts of toluene are employed. If the reaction is carried out on an industrial scale very long reaction times and distillation times are required, if only because of the continuous azeotropic distillation with toluene. The excess of formaldehyde, required to give substantially quantitative conversion, forms deposits on the condenser whilst the water of reaction is being removed from the system, and causes blockages in the reaction kettles and pipelines. To avoid such deposits, the condenser must be flushed continuously with water which must then, together with the water of reaction removed azeotropically, be separated from the entraining agent in a water separator. Since formaldehyde caking occurs in the reaction kettle, it is necessary to circulate the entire reaction mixture, by pumping, during the process of removing the water from the system. In addition, the process can only be carried out with the relatively stable anilines which are substituted in the 2-position or, more particularly, in the 2- and 6-positions, by groups which cause steric hindrance, for example tert.-butyl groups; the patent does not mention the preparation of the interesting anilines which are substituted in the 2- and 6-positions by unbranched, and more particularly lower, alkyl groups.

We have found that aromatic azomethines of the formula

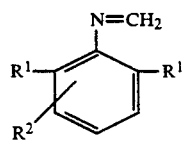
I where the individual radicals $R^1$ and $R^2$ may be identical or different and each is halogen, an aliphatic radical or alkoxy, and $R^2$ may also be hydrogen, are obtained in an advantageous manner by reacting an aromatic amine with formaldehyde, if an aniline of the formula

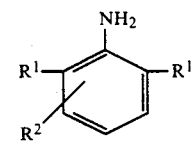
II where $R^1$ and $R^2$ have the above meanings, is reacted with formaldehyde and thereafter at least 98 percent by weight of the total amount of water is removed from the reaction mixture by distillation under a pressure of less than 500 mbar, the distillation, and, if desired, the reaction or a part thereof, being carried out in the presence of from 0.5 to 30 percent by weight, based on starting material II, of an alcohol having a boiling point below 160° C.

Where 2,6-dimethylaniline is used, the reaction may be represented by the following equation:

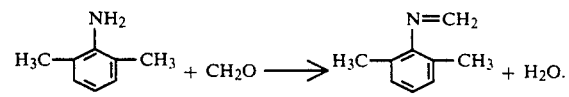

Compared to the conventional processes, the process according to the invention gives aromatic azomethines more simply and more economically, and in better space-time yield. The use of aromatic hydrocarbons, especially those of carcinogenic character, as solvents is avoided.

In the process according to the invention, the reaction is as a rule carried out without an organic solvent; the process causes less pollution of the environment, and is safer than when carried out in the conventional manner in the presence of a solvent. The reaction time and the distillation time are substantially shorter than in the conventional process. Deposition of formaldehyde in parts of the apparatus, with consequent operating problems, or even stoppages, is avoided, without having to take expensive safety measures. All these advantages of the novel process are surprising in view of the prior art. In particular, the process can also be used to prepare the interesting anilines which are substituted in the 2- and 6-positions by unbranched, more particularly lower, alkyl groups.

The starting materials are reacted with one another in stoichiometric amounts or using an excess of formaldehyde, preferably from 1 to 3, especially from 1.1 to 1.4, moles of formaldehyde per mole of starting material II. The formaldehyde is advantageously employed as a gas or as a compound which forms formaldehyde under the reaction conditions, eg. paraformaldehyde or trioxane. Preferred starting materials II, and accordingly preferred end products I, are those where the individual radicals $R^1$ and $R^2$ are identical or different and are each chlorine, bromine, alkyl, especially unbranched alkyl, alkoxy or perhaloalkyl, especially perfluoroalkyl or perchloroalkyl, in each case of 1 to 7 carbon atoms, or alkoxyalkyl of 2 to 7 carbon atoms, and $R^2$ may also be hydrogen. The above radicals may in addition be substituted by groups which are inert under the reaction conditions, eg. alkyl or alkoxy, each of 1 to 4 carbon atoms.

Accordingly, examples of suitable starting materials II are the following anilines: 2,6-dimethyl-, 2,6-diethyl-, 2,6-dipropyl-, 2,6-diisopropyl-, 2,6-ditert.-butyl-, 2,6-dibutyl-, 2,6-di-sec.-butyl-, 2,6-diisobutyl-, 2,6-dichloro-, 2,6-dibromo, 2,6-dimethoxy-, 2,6-diethoxy-, 2,6-dipropoxy-, 2,6-diisopropoxy-, 2,6-dibutoxy-, 2,6-di-sec.-butoxy-, 2,6-di-tert.-butoxy, 2,6-diisobutoxy-, 2,6-ditrifluoromethyl-, 2,6-dichloromethyl-, 2,6-diethoxymethyl-, 2,6-diethoxyethyl-, 2,6-dimethoxymethyl-, 2,6-dimethoxyethyl-, 2-ethyl-6-methyl-, 2-methyl-6-chloro-, 2-methyl-6-bromo-, 2-methyl-6-propyl- and 2-ethyl-6-propyl-aniline, and corresponding anilines which are additionally substituted in the 3-, 4- or 5-position by methyl, ethyl, propyl, isopropyl, butyl, isobutyl, sec.-butyl, tert.-butyl, methoxy, ethoxy, propoxy, isopropoxy, butoxy, isobutoxy, sec.-butoxy, tert.-butoxy, chlorine, bromine, trifluoromethyl or trichloromethyl.

The reaction is in general carried out at from 60° to 140° C., especially from 70° to 100° C., under atmospheric or superatmospheric pressure, continuously or batchwise, and as a rule without addition of an organic solvent and without addition of water. The water formed during the reaction is left in the reaction mixture. It is a surprising, essential and advantageous feature of the invention that the water of reaction is only distilled off when the reaction is substantially complete.

In general, the alcohol is only added to the reaction mixture after completion of the reaction and before commencing the distillation. If desired, however, the alcohol can also be added to the reaction mixture during the reaction, or be added to the starting mixture ab initio.

In a preferred embodiment, the reaction is carried out in the absence of a solvent and without addition of alcohol, merely in the presence of the water of reaction which is formed, the total amount of alcohol is then added, and the distillation is carried out thereafter. The alcohols used advantageously boil below 160° C., preferably at from 65° to 120° C., especially from 65° to 85° C., and are advantageously alkanols and cycloalkanols, especially alkanols of 1 to 5 carbon atoms. Examples of suitable alcohols are isopropanol, ethanol, n-propanol, tert.-butanol, sec.-butanol, n-hexanol, n-butanol, isobutanol, cyclohexanol, n-pentanol, pentan-2-ol and 2,3-dimethylpentan-1-ol. Methanol is preferred. From 0.5 to 30, preferably from 5 to 25, advantageously from 10 to 20, percent by weight of alcohol, based on starting material II, is used.

The reaction may be carried out as follows: a mixture of starting material II and formaldehyde, advantageously in the form of paraformaldehyde, is kept at the reaction temperature for from 0.5 to 3 hours. The alcohol is then added and the distillation of the water is commenced.

The distillation is carried out under a pressure of less than 500 mbar, advantageously from 50 to 400 mbar, especially of from 80 to 200 mbar, in general at from 60° to 200° C., especially from 80° to 160° C., continuously or batchwise. At least 98, advantageously from 98 to 100, especially from 99.5 to 100, percent by weight of the total amount of water is removed from the reaction mixture by the distillation process.

The residue left after the distillation is crude end product I, which as a rule is from 90 to 98 percent by weight pure. The pure end product I may be obtained in a conventional manner, for example by fractional distillation. In general, however, it is advantageous to use the end product, as obtained, for further conversion. In that case it is advantageous to dilute the distillation residue with a solvent suitable for the subsequent synthesis, for example with toluene, and to feed this end product solution to the further conversion process.

The aromatic azomethines I obtainable by the process of the invention are valuable starting materials for the preparation of herbicides, especially pre-emergence and post-emergence herbicides, fungicides, insecticides, bacteriostatic agents, fungistatic agents and vulcanization accelerators. Regarding their use, reference may be made to German Published Application DAS No. 1,793,811.

In the Examples which follow, parts are by weight.

EXAMPLE 1

24.2 parts of 2,6-dimethylaniline and 7.8 parts of paraformaldehyde are introduced into a stirred apparatus and heated to 80° C. in ½ hour. The mixture is stirred at this temperature for 30 minutes and then cooled to 60° C., and 3.2 parts of methanol are added. A mixture of water (3.5 parts), methanol (3 parts) and formaldehyde (1 part) is then distilled from the reaction mixture under a pressure of 150 mbar. After one hour, the bottom temperature has reached 100° C. The reaction mixture is kept at this temperature for a further 15 minutes, after which the vacuum is released and 50 parts of toluene are added. According to gas-chromatographic analysis, 25.8 parts (97% of theory) of N-(2,6-dimethylphenyl)-N-methyleneimine of boiling point 96°-104° C./34 mbar are obtained.

EXAMPLE 2

270 parts of 2-ethyl-6-methylaniline and 78 parts of paraformaldehyde are stirred for 30 minutes at 90° C. in a vessel equipped with a stirrer. The mixture is then cooled to 70° C. and 32 parts of methanol are added. A mixture of methanol (31 parts), water (37 parts) and formaldehyde (11 parts) is then distilled off under 150 mbar, and whilst doing so the bottom temperature rises to 125° C. in the course of one hour. The mixture is kept at this temperature for 10 minutes and is then diluted with 600 parts of toluene, under 760 mbar. According to gas-chromatographic analysis, 289 parts (95% of theory) of N-(2-ethyl-6-methylphenyl)-N-methyleneimine of boiling point 78°-80° C./5 mbar are obtained.

EXAMPLE 3

149 parts of 2,6-diethylaniline and 39 parts of paraformaldehyde are reacted as described in Example 1. According to gas-chromatographic analysis, 154.5 parts (96% of theory) of N-(2,6-diethylphenyl)-N-methyleneimine of boiling point 105°-106° C./14 mbar are obtained.

We claim:

1. A process for the preparation of aromatic azomethines of the formula

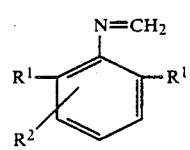

where the individual radicals $R^1$ and $R^2$ may be identical or different and each is halogen, an aliphatic radical or alkoxy, and $R^2$ may also be hydrogen, by reacting an aromatic amine with formaldehyde; wherein an aniline of the formula

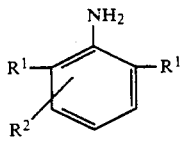

where $R^1$ and $R^2$ have the above meanings, is reacted with formaldehyde in the absence of a solvent and without the addition of alcohol, and thereafter, when the reaction is substantially complete, at least 98 percent by weight of the total amount of water is removed from the reaction mixture by distillation being carried out in the presence of from 0.5 to 30 percent by weight, based on starting material II, of an alcohol having a boiling point below 160° C.

2. The process of claim 1, wherein the reaction is carried out with from 1 to 3 moles of formaldehyde per mole of starting material II.

3. The process of claim 1, wherein the reaction is carried out at from 60° to 140° C.

4. The process of claim 1 or claim 2, wherein the alcohol has a boiling point from 65° to 120° C.

5. The process of claim 1, wherein the distillation is carried out with from 5 to 25 percent by weight of alcohol, based on starting material II.

6. The process of claim 1, wherein the distillation is carried out under a pressure of from 50 to 400 mbar.

7. The process of claim 1, wherein the distillation is carried out so as to remove from 98 to 100 percent by weight of the total amount of water from the reaction mixture.

* * * * *